United States Patent [19]

Moore et al.

[11] 4,342,751

[45] Aug. 3, 1982

[54] MAJUSCULAMIDE C

[75] Inventors: Richard E. Moore, Honolulu, Hi.; Jon S. Mynderse, Indianapolis, Ind.

[73] Assignee: Eli Lilly and Company, Indianapolis, Ind.

[21] Appl. No.: 241,812

[22] Filed: Mar. 9, 1981

[51] Int. Cl.$^3$ .................... A61K 37/00; C07C 103/52
[52] U.S. Cl. ............................... 424/177; 260/112.5 R
[58] Field of Search ................. 424/177; 260/112.5 R

[56]  References Cited
PUBLICATIONS

D. C. Carter, Marine Natural Products: The Structure of an Unusual Cyclic Depsipeptide from *Lyngbya majuscula*, a thesis presented to the graduate division of the University of Hawaii, Dec., 1980.
J. S. Mynderse et al., Antileukemia Activity in the Oscillatoriaceae: Isolation of Debromoaplysiatoxin from Lyngbya, *Science* 196, 538-540, (Apr. 29, 1977).
R. E. Moore, Toxins from Blue-Green Algae, *BioScience* 27 (12), 797-802, (1977).
R. E. Moore, High Frequency NMR Studies of Some Marine Natural Products, Abstracts, 6th International Symposium on Magnetic Resonance, Banff, Canada, p. 124.
F. Marner et al., Majusculamides A and B, Two Epimeric Lipodipeptides From *Lyngbya majuscula* Gomont, *J. Org. Chem.* 42, 2815-2819 (1977).
J. S. Mynderse et al., Malyngamides D and E, Two trans-7-Methoxy-9-methylhexade-4-enamides from a Deep Water Variety of the Marine Cyanophyte *Lyngbya majuscula*, *J. Org. Chem.* 43, 4359 (1978).
R. E. Moore, Grant Proposal entitled "Natural Products From Marine Organisms", and Correspondence With National Science Foundation for Grant No. CHE79-25416.
R. L. Pecsok, Grant Proposal entitled "Purchase of 300 MHz Fourier Transform Superconductive Magnet Nuclear Magnetic Resonance Spectrometer", submitted to the National Science Foundation, title pages and pp. 44-45.
J. C. Braekman et al., III International IUPAC Symposium on Marine Natural Products: a Survey, *Trends in Pharmacol. Sciences* 2, VII-VIX (Feb. 1981).
K. L. Rinehart, Jr., et al., Didemnins: Antiviral and Antitumor Depsipeptides From a Caribbean Tunicate, *Science* 212, 933-935 (May 22, 1981).

*Primary Examiner*—Phillips Delbert R.
*Attorney, Agent, or Firm*—Nancy J. Harrison; Arthur R. Whale

[57]  ABSTRACT

Majusculamide C, a novel cyclic peptide compound which inhibits fungal plant pathogens, process for its preparation from a deep-water blue-green alga, *Lyngbya majuscula*, and process for inhibiting fungal plant pathogens with and fungicidal compositions containing majusculamide C.

4 Claims, 1 Drawing Figure

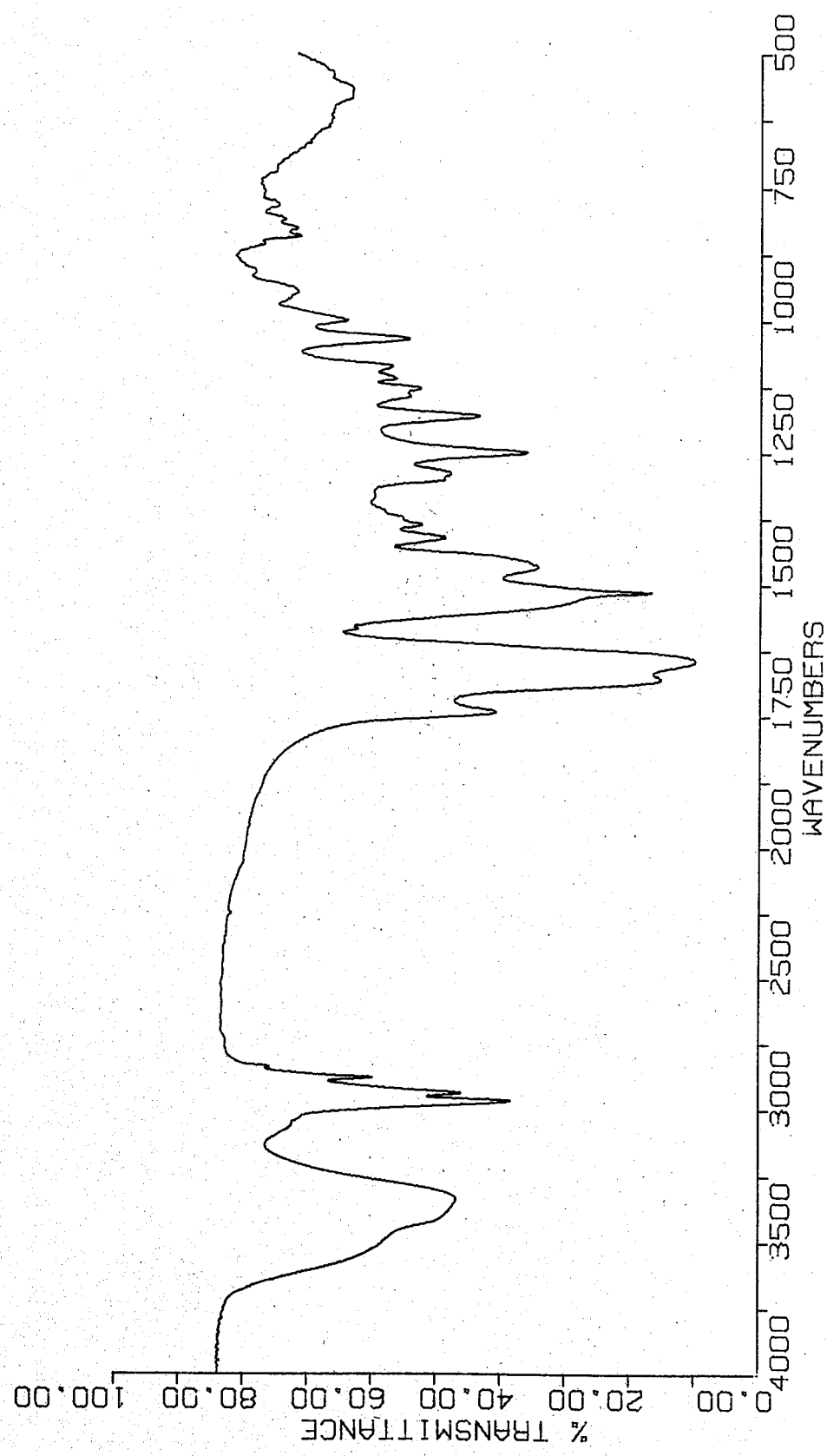

MAJUSCULAMIDE C

The Government has rights in this invention pursuant to Grant No. CHE 79-25416 awarded by the National Science Foundation.

SUMMARY OF THE INVENTION

This invention relates to a new cyclic peptide which is designated majusculamide C. We have found that majusculamide C is contained in marine organisms, in particular in an algal association, the primary constituent of which is the blue-green alga *Lyngbya majuscula*. This algal association can be collected from Pinnacles in Enewetak lagoon at Enewetak atoll, which is located in the Marshall Islands.

Accordingly, this invention relates in one aspect to the isolation of majusculamide C from natural sources, especially marine organisms, particularly a deep-water strain of blue-green alga of the species *Lyngbya majuscula*. Majusculamide C in substantially pure form, i.e., free from naturally occurring byproducts, is a further feature of the present invention. In other aspects, this invention relates to the use of majusculamide C to inhibit fungal plant pathogens and to fungicidal compositions containing majusculamide C.

DESCRIPTION OF THE DRAWING

The infrared spectrum of majusculamide C, run in KBr disc, is provided in the accompanying drawing.

DETAILED DESCRIPTION OF THE INVENTION

Fungal plant pathogens cause great economic losses each year. New agents effective against these phytopathogens are needed. Presently used fungicides differ in their effectiveness against specific fungi. In addition, resistant fungal strains frequently develop, creating a continual need for new, effective agents.

This invention provides a new cyclic peptide compound which is designated majusculamide C. Majusculamide C is useful against a number of fungal plant pathogens such as, for example, tomato late blight and grape downy mildew.

Majusculamide C has thus far been found in an algal association, the primary constituent of which is a deep-water seaweed of the family Oscillatoriaceae, the blue-green alga *Lyngbya majuscula*. The term "deep water" used herein refers to depths of from about 25 to about 100 feet. This term is used to distinguish the algal association of this invention from *Lyngbya majuscula* found in the shallow waters, i.e. depths of less than about 20 feet, of Enewetak lagoon. The shallow-water Lyngbya found there do not contain majusculamide C.

The alga of this invention is found in the lagoon at Enewetak atoll in the Marshall Islands. In addition to majusculamide C, the alga produces a toxin, debromoaplysiatoxin, which causes a severe contact dermatitis called "swimmer's itch". [see Mynderse et al., *Science* 196, 538-540 (1977)]. This toxin is separated from majusculamide C by chromatography.

Majusculamides A and B are major lipophilic constituents of several shallow-water varieties of *Lyngbya majuscula* found in Hawaii and Enewetak [see Marner et al., *J. Org. Chem.* 42, 2815-2819 (1977)]. Majusculamide B is N-[(S)-2-methyl-3-oxodecanoyl]-D-N,O-dimethyltyrosyl-L-N-methylvalinamide. Majusculamide A is the (2R)-2-methyl-3-oxodecanoyl epimer of majusculamide B. Majusculamides A and B were not found in the deep-water *L. majuscula* which contained majusculamide C.

Majusculamide C can be isolated from the natural source, e.g., from the blue-green alga *Lyngbya majuscula*, using techniques which will be apparent to those skilled in the art. For example, a preferred method of isolating majusculamide C is to extract the freeze-dried alga exhaustively with hexane, acetone, and methanol. The organic solvents are then combined and evaporated to give an extract. The extract is partitioned between hexane and 90% aqueous methanol. The methanolic portion is then partitioned between dichloromethane and 80% aqueous methanol. The dichloromethane portion is chromatographed over Sephadex (LH-20) to give majusculamide C which can be further purified by high performance liquid chromatography (HPLC).

Majusculamide C is a white amorphous solid which has a molecular weight of approximately 984, based on field-desorption mass spectral data.

Majusculamide C is soluble in solvents such as methanol, dichloromethane, and acetone but is not soluble in water. The specific optical rotation, $[\alpha]_D$, of majusculamide C is $-96°$ (c 2.5, $CH_2Cl_2$).

The infrared (IR) spectrum of majusculamide C in KBr disc is shown in the accompanying drawing. The IR spectrum has the following absorption maxima:

| Wavenumber (cm$^{-1}$) | Percent Transmittance |
|---|---|
| 3336.13 | 46.73 |
| 2967.70 | 38.329 |
| 2937.80 | 46.061 |
| 2878.97 | 53.83 |
| 2837.49 | 68.28 |
| 1741.85 | 40.857 |
| 1680.12 | 15.247 |
| 1643.47 | 9.872 |
| 1585.60 | 56.29 |
| 1514.23 | 16.761 |
| 1465.04 | 34.352 |
| 1411.03 | 43.91 |
| 1385.95 | 47.18 |
| 1373.42 | 49.82 |
| 1357.98 | 52.62 |
| 1301.08 | 44.04 |
| 1289.51 | 43.16 |
| 1249.00 | 36.099 |
| 1180.52 | 43.466 |
| 1142.91 | 48.76 |
| 1127.47 | 47.32 |
| 1109.15 | 50.70 |
| 1086.93 | 51.31 |
| 1033.92 | 49.04 |
| 1000.16 | 57.66 |
| 946.15 | 64.56 |
| 908.54 | 70.48 |
| 857.42 | 69.30 |
| 841.99 | 64.20 |
| 827.52 | 64.63 |
| 812.09 | 66.6 |
| 783.16 | 67.19 |

The ultraviolet absorption spectrum of majusculamide C in ethanol shows absorption maxima at 278 nm ($\epsilon$ 1420) and 230 nm ($\epsilon$ 5900).

$^1$H and $^{13}$C nuclear magnetic resonance (NMR) spectral and mass spectral analyses indicate that the molecular composition of majusculamide C is $C_{50}H_{80}N_8O_{12}$. Nuclear magnetic resonance analysis also shows that two glycyl units, one alanyl unit, one N-methylvalyl unit, and one N,O-dimethyltyrosyl unit are present. Acid hydrolysis (1.5 N HCl, 25% ethanol-water, reflux 24 hours) of majusculamide C leads to L-alanine, glycine, L-N-methylvaline, L-N-O-dimethyltyrosine, L-N-methylisoleucine, 2-hydroxy-3-methylpentanoylglycine, 2-amino-3-oxo-4-methylpentane (isolated as the hydrochloride), and 3-amino-2-methylpentanoic acid. Thus, the following eight sub-units (1a through 1h) account for all the atoms in the molecular formula of majusculamide C:

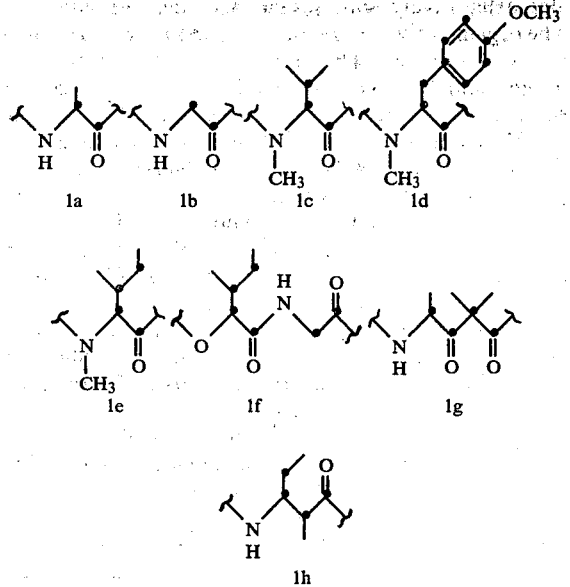

Table 1 gives the $^1$H NMR data for majusculamide C at 360 MHz.

TABLE 1

| $^1$H NMR Signals of Majusculamide C | | |
|---|---|---|
| Chemical Shift* | | Multiplicity** |
| 7.767 | | d, J = 8.1 Hz |
| 7.573 | | d, J = 7.4 Hz |
| 7.355 | | t, J = 5.4 Hz |
| 7.309 | | d, J = 6.7 Hz |
| 7.129 | 2H, | d, J = 8.5 Hz |
| 7.068 | | d, J = 10.2 Hz |
| 6.834 | 2H | d, J = 8.5 Hz |
| 5.186 | | d, J = 3.2 Hz |
| 5.132 | | t, J = 7.3 Hz |
| 4.893 | | p, J = 6.8 Hz |
| 4.888 | | d, J = 11.1 Hz |
| 4.777 | | d, J = 10.7 Hz |
| 4.606 | | dd, J = 8.3, 17.7 Hz |
| 4.509 | | tdd, J = 10.2, 5.7, 2.7 Hz |
| 4.437 | | dd, J = 15.9, 5.4 Hz |
| 4.401 | | dd, J = 2.1, 6.7 Hz |
| 3.738 | 3H, | s |
| 3.541 | | dd, J = 15.9, 5.0 Hz |
| 3.445 | | dd, J = 17.6, 1.0 Hz |
| 3.237 | | dd, J = 14.2, 7.0 Hz |
| 3.201 | 3H, | s |
| 2.944 | 3H, | s |
| 2.938 | 3H, | s |
| 2.792 | | dd, J = 8.1, 14.0 Hz |
| 2.735 | | dq, J = 2.6, 7.0 Hz |
| 2.250 | | ds, J = 10.7, 6.7 Hz |
| 2.206 | 2H, | m |
| 1.508 | 3H, | s |
| 1.2–1.6 | 6H, | m |
| 1.462 | 3H, | s |
| 1.136 | 3H, | d, J = 6.8 Hz |
| 1.082 | 3H, | d, J = 7.0 Hz |
| 1.042 | 3H, | d, J = 6.6 Hz |
| 1.024 | 3H, | d, J = 6.2 Hz |
| 0.916 | 3H, | d, J = 7.4 Hz |
| 0.873 | 3H, | d, J = 7.5 Hz |
| 0.862 | 6H, | t, J = 7.7 Hz |
| 0.738 | 3H, | d, J = 6.6 Hz |

TABLE 1-continued

| $^1$H NMR Signals of Majusculamide C | |
|---|---|
| Chemical Shift* | Multiplicity** |
| 0.393 | 3H, d, J = 6.5 Hz |

*Chemical shifts are the values in chloroform-d in ppm.
A signal represents one proton unless otherwise described.
**s = singlet, d = doublet, dd = doublet of doublets, tdd = triplet of doublets of doublets, dq = doublet of quartets, ds = doublet of septets, p = pentet.

The $^{13}$C NMR data for majusculamide C are listed in Table 2.

TABLE 2

| $^{13}$C NMR Signals of Majusculamide C in Deuteriochloroform* | | | | |
|---|---|---|---|---|
| 209.97(s) | 158.58(s) | 55.06(s) | 32.63(d) | 18.95(q) |
| 172.64(s) | 130.28(d) | 54.72(s) | 30.17(s) | 18.32(q) |
| 172.46(s) | 130.28(d) | 51.45(d) | 29.08(s) | 18.27(q) |
| 171.90(s) | 128.55(s) | 51.07(d) | 29.04(s) | 15.31(q) |
| 170.91(s) | 114.15(s) | 48.15(d) | 26.86(d) | 15.30(q) |
| 170.12(s) | 114.15(s) | 42.36(d) | 25.85(t) | 15.30(q) |
| 169.99(s) | 78.20(d) | 40.62(t) | 24.80(t) | 11.48(q) |
| 169.86(s) | 60.98(d) | 40.45(t) | 23.62(t) | 10.80(q) |
| 169.21(s) | 60.86(d) | 37.20(d) | 21.98(q) | 9.88(q) |
| 167.85(s) | 57.98(d) | 34.46(t) | 21.30(q) | 9.60(q) |

*Chemical shifts are expressed in ppm. The multiplicity is in parentheses.

Table 3 lists conclusions which can be drawn about the structure of majusculamide C based on the $^1$H NMR and $^{13}$C NMR spectra.

TABLE 3

| Structural Conclusions for Majusculamide C from $^1$H NMR and $^{13}$C NMR Spectra | |
|---|---|
| Chemical Shift | Number and Kinds of Carbons |
| 209.97 | 1 Ketone carbonyl |
| 167.85, 169.21, 169.86, 169.99, 170.12, 170.91, 171.90, 172.46, 172.64 | 9 Amide/ester carbonyls |
| 128.55, 158.58 | 2 Aromatic tertiary carbons |
| 114.15(2), 130.28(2) | 4 Aromatic methine carbons |
| 55.06 | 1 Methoxy |
| 29.04, 29.08, 30.17 | 3 N-methyls |
| 54.72 | 1 Tertiary carbon |
| 26.86, 32.63, 37.20, 42.36, 48.15, 51.07, 51.45, 57.98, 60.86, 60.98, 78.20 | 11 Methines |
| 23.62, 24.80, 25.85, 34.46, 40.45, 40.62 | 6 Methylenes |
| 9.60, 9.88, 10.80, 11.48, 15.30, 15.30, 15.31, 18.27, 18.32, 18.95, 21.30, 21.98 | 12 Methyls |

Electron-impact mass spectrometry (low resolution) analysis of majusculamide C gives the following fragmentation pattern, m/z (rel intensity): 757(5), 756(13), 597(14), 596(38), 566(21), 565(62), 508(2), 452(6), 396(19), 395(80), 381(2), 324(2), 275(9), 248(5), 211(6), 204(28), 164(12), 161(19), 155(12), 121(13), 114(100%).

The observed and calculated fragments of majusculamide C on high resolution electron impact mass spectroscopy are summarized in Table 4.

TABLE 4

| High Resolution Mass Spectral Data of Majusculamide C | | |
|---|---|---|
| | Calculated | Observed |
| $C_{12}H_{19}O_3$ | 211.13342 | 211.1327 |
| $C_{17}H_{26}O_5N$ | 324.18108 | 324.1786 |
| $C_{21}H_{35}O_5N_2$ | 395.25458 | 395.2529 |
| $C_{23}H_{38}O_6N_3$ | 452.27606 | 452.2730 |
| $C_{29}H_{49}O_7N_4$ | 565.36013 | 565.3570 |
| $C_{40}H_{62}O_9N_5$ | 756.45476 | 756.4455 |

Sequencing based on the mass spectral data suggests that a glycyl-N-methylisoleucylglycyl-N-methylvalyl-N,O-dimethyltyrosyl sequence is present in majusculamide C.

Majusculamide C has a retention time of approximately 14.7 minutes on high performance liquid chromatography (HPLC), using a Dupont Zorbax C-8 4.6-mm×25-cm column, an acetonitrile:water (15:85) mobile phase, and a flow rate of 2 ml per minute.

Based on the characteristics known thus far, the structure shown in formula 2 has been postulated as the tentative structure for majusculamide C:

This invention also relates to a method of protecting plants from phytopathogenic fungi which comprises contacting the loci of the fungi with a fungicidally-effective amount of majusculamide C. The loci of the fungi can be a portion of the plant, such as leaves, stems, flowers or roots, or the soil wherein the fungi may be located. Majusculamide C appears to translocate from roots to shoots; consequently it is possible that application could be made to seeds, roots, etc. to obtain fungicidal effect throughout the plant. Application rates will vary according to a number of factors, such as the location of the plants being protected and the severity of the fungal infection. Thus, for use in a greenhouse, the fungicidal compound is applied as a soil drench using a composition having a concentration in the range of from about 1 to about 200 ppm of active ingredient, preferably from about 5 to about 100 ppm. As is understood by those in the art, application rates used in the field are usually greater than those used in a greenhouse, and range from about 25 to about 1000 ppm.

Majusculamide C has been shown by suitable tests to control a number of fungi, including *Phytophthora infestans*, the causative organism of tomato late blight, *Plasmopora viticola*, the causative organism of grape downy mildew and *Rhizoctonia solani*, the causative organism of Rhizoctonia damping-off.

In another embodiment, this invention relates to compositions suitable for inhibiting plant-pathogenic fungi comprising (1) majusculamide C in an amount effective to inhibit the growth of a plant-pathogenic fungus and (2) a suitable carrier.

The compositions for use in this embodiment desirably contain, in addition to the majusculamide C, one or more of a plurality of additaments including water, polyhydroxy compounds, petroleum distillates, and other dispersion media, surface-active dispersing agents, emulsifiers, and finely-divided inert solids. The concentration of majusculamide C in these compositions will vary depending on whether the composition is intended for direct application to plants or is intended to be subsequently diluted with additional inert carrier such as water to produce the ultimate treating composition.

Treating compositions are most conveniently formulated by preparing liquid or solid concentrates, which are subsequently diluted to the desired level for use. Emulsifiable liquid concentrates can be prepared by incorporating from about 1 to about 10 percent by weight of the active ingredient and an emulsifiable agent in a suitable water-immiscible organic liquid. Such concentrates may be further diluted with water to form spray mixtures in the form of oil-in-water emulsions. Such spray compositions then comprise active compound, water-immiscible solvent, emulsifying agent, and water. Suitable emulsifying agents can be of the nonionic or ionic types, or blends thereof, and include condensation products of alkylene oxides with phenols and organic acids, polyoxyethylene derivatives of sorbitan esters, complex ether alcohols, ionics of the arylalkyl sulfonate type, and the like. Suitable water-immiscible organic liquids include aromatic hydrocarbons, aliphatic hydrocarbons, cycloaliphatic hydrocarbons, and mixtures thereof such as petroleum distillates.

Solid concentrate mixtures can be prepared by incorporating from about 10 to about 50% by weight of active compound in a finely-divided solid carrier such as bentonite, Fuller's earth, diatomaceous earth, hydrated silica, diatomaceous silica, expanded mica, talc, chalk, and the like. Such concentrates can be formulated, if desired, for direct use as dusting compositions, or can be diluted, if desired, with additional inert solid carriers to produce dusting powders containing around 0.05 to 1% by weight of majusculamide C. Alternatively, the surfactants, that is, dispersing and/or wetting agents, can be incorporated along with majusculamide C in the solid carrier to form wettable powder concentrates ranging from about 10 to about 25% by weight concentration, which subsequently can be dispersed in water or other hydroxylated carrier to form spray compositions. Suitable surfactants include condensed aryl sulfonic acids and sodium salts thereof, sodium lignosulfate, sulfonate-oxide condensate blends, alkylaryl polyether alcohols, sulfonate/nonionic blends, anionic wetting agents, and the like.

Further, majusculamide C can be incorporated in solutions, simple dispersions, aerosol formulations, and other media acceptable for treating vegetation or for applying to the soil.

The antifungal composition of this embodiment is applied to infected or susceptible plant or soil surfaces in any convenient fashion such as by spraying, dusting, dipping, or drenching. A spray method is considered preferable, especially when large numbers of plants are involved, because such a treatment is faster and more uniform. In spraying it is usually sufficient for the infected or susceptible surfaces to be made thoroughly wet with the liquid dispersion. Good results can be obtained by using spray compositions whether they are emulsions or aqueous dispersions of solid concentrates.

Where the fungi to be controlled are in the soil, the antifungal compound can be applied to the soil directly, or it can be diluted with various inert solid or liquid diluents and then applied to the soil. In one method of application the soil surface is sprayed with a liquid dispersion or emulsion of the active ingredient. The application is allowed to remain as a coating on the surface of the soil or, alternatively, is incorporated into the soil by disking, hoeing, or other methods known to those in the art. Another method of application is to apply the active ingredient in the form of a liquid dispersion or emulsion to the soil as a drench. Thus, for the control of soil-inhabiting fungi in the greenhouse, the application rate varies from about 5 to about 200 ppm active ingredient.

Majusculamide C can also be used as a seed soak for seeds prior to planting. A suitable seed soak formulation contains majusculamide C together with excipients such as a mixture of ethanol-acetone, polyoxyethylene sorbitan monolaurate, and the like.

When used as a seed soak, control can be accomplished at an application rate of from about 50 to about 400 ppm of majusculamide C. The seeds are allowed to soak in the formulation for about 4 hours and then are removed and planted.

The activity of majusculamide C against plant pathogenic fungi in standard in vitro agar-dilution tests is summarized in Tables 5-10. In these tests 100× solutions of majusculamide C in 95% aqueous ethanol were used. Majusculamide C solution (0.1 ml) and melted agar (9.9 ml) at 50° C. were mixed. An inoculum plug (6-mm diameter) was placed in the center of each plate; the radial growth of the colony was measured. Zone of growth was measured from the edge of the plug to the edge of the colony.

TABLE 5

In Vitro Agar Dilution Activity of Majusculamide C

| Majusculamide C Level (ppm) | Rhizoctonia solani | | Sclerotinia homoeocarpa | | Pythium aphanidermatum | |
|---|---|---|---|---|---|---|
| | Zone of Growth | Percent Inhibition | Zone of Growth | Percent Inhibition | Zone of Growth | Percent Inhibition |
| 1 | 19 | 30 | 17 | 26 | 1 | 97 |
| 10 | 10 | 63 | 16 | 30 | 0 | 100 |
| $0^a$ | 27 | 0 | 23 | 0 | 28 | 0 |

[a] Control

The $ED_{50}$ (effective dose to achieve 50% inhibition) values for majusculamide C against the organisms in Table 5, calculated using the results given there, are summarized in Table 6.

TABLE 6

| $ED_{50}$ Values for Majusculamide C | |
|---|---|
| Organism | $ED_{50}$ |
| Rhizoctonia solani | 4 ppm |
| Sclerotinia homoeocarpa | >10 ppm |
| Pythium aphanidermatum | <1 ppm |

TABLE 7

In Vitro Agar-Dilution Activity of Majusculamide C and Ridomil

| Compound | Level (ppm) | Pythia aphanidermatum | | Aphanomyces euteiches | | Phytophthora infestans | |
|---|---|---|---|---|---|---|---|
| | | Zone of Growth | Percent Inhibition | Zone of Growth | Percent Inhibition | Zone of Growth | Percent Inhibition |
| Majusculamide C | 0.01 | 30 | 6 | 27 | 7 | 10 | 17 |
| " | 0.1 | 12 | 62 | 27 | 7 | 7 | 42 |
| " | 1.0 | 1.5 | 95 | 20.5 | 29 | 6.5 | 46 |
| " | 10.0 | 0 | 100 | 3.5 | 88 | 0 | 100 |
| Ridomil (tech.) | 0.1 | 21 | 34 | 27 | 7 | 6 | 50 |
| " | 1.0 | 2 | 94 | 28 | 3 | 2 | 83 |
| Control | 0 | 32 | 0 | 29 | 0 | 12 | 0 |

The $ED_{50}$ values for majusculamide C against the organisms in Table 7, calculated using the results given there, are summarized in Table 8.

TABLE 8

| $ED_{50}$ Values for Majusculamide C | |
|---|---|
| Organism | $ED_{50}$ |
| Pythium aphanidermatum | 0.07 ppm |
| Aphanomyces euteiches | 2.1 ppm |
| Phytophthora infestans | 1.07 ppm |

In Table 9 the activity of majusculamide C against two Ridomil-sensitive and two Ridomil-resistant strains is compared.

TABLE 9

In Vitro Activity of Majusculamide C Against Ridomil-Resistant Strains

| Majusculamide C Level (ppm) | Pythium ultimum | | | | Phytophthora capsici | | | |
|---|---|---|---|---|---|---|---|---|
| | Ridomil-sensitive strain | | Ridomil-resistant strain[a] | | Ridomil-Sensitive strain | | Ridomil-resistant strain[a] | |
| | Zone of Growth | Percent Inhibition | Zone of Growth | Percent Inhibition | Zone of Growth | Percent Inhibition | Zone of Growth | Percent Inhibition |
| 0.1 | 18.5 | 53 | 15.5 | 60 | 14.5 | 46 | 14.5 | 48 |
| 1 | 4.5 | 88 | 3.5 | 91 | 7 | 74 | 4.5 | 84 |
| 10 | 0 | 100 | $0^b$ | 100 | 0 | 100 | 0.5 | 98 |
| $0^c$ | 39 | 0 | 39 | 0 | 27 | 0 | 28 | 0 |

[a] Maintained on V-8 agar with 100 ppm Ridomil
[b] No growth on plug
[c] Control The ED$_{50}$ values for majusculamide C against the organisms in Table 9, calculated using the results given there, are summarized in Table 10.

TABLE 10

| ED$_{50}$ Values for Majusculamide C Against Ridomil-Resistant Strains | |
|---|---|
| Organism | ED$_{50}$ (ppm) |
| Pythium ultimum (Ridomil-sensitive) | <0.1 |
| Pythium ultimum (Ridomil-resistant) | <0.5 |
| Phytophthora capsici (Ridomil-sensitive) | 0.45 |
| Phytophthora capsici (Ridomil-resistant) | 0.25 |

Majusculamide C was effective when tested in vivo against *Phytophthora infestans*, the causative agent of tomato late blight, and *Plasmopora viticola*, the causative agent of grape downy mildew. In these tests majusculamide C was formulated in a solvent of acetone:ethanol (1:1) plus 0.05% Tween 20. Tomato leaves (C. V. Rutgers) were placed, top side up, on rubber mats in Petri dishes. Grape leaves (C. V. Niagara) were placed, bottom side up, on filter paper on rubber mats in Petri dishes. Foliar spray solutions of test compounds were placed on the leaves, using two replicates per dosage per leaf type. Leaves were dried, and water (approximately 10 ml) was added to the bottom of the Petri dish. Tomato leaves were inoculated with a zoospore suspension of *P. infestans*. Grape leaves were inoculated with a sporangial suspension of *P. viticola*. Tomato leaves were incubated in a 15° C. incubator for 48 hr and then at room temperature for 5 days. Grape leaves were incubated in a lighted chamber at 20° C. for 7 days.

Leaves were rated on a 1-5 scale wherein 1=severe disease and 5=no disease. Phytotoxicity was also rated on a 1-5 scale with 0=no injury and 5=severe injury. Table 11 summarizes the results of these tests.

TABLE 11.

In Vivo Activity of Majusculamide C

| | Disease Ratings[a] | | | |
|---|---|---|---|---|
| | Tomato Late Blight | | Grape Downy Mildew | |
| Majusculamide C Dosage (ppm) | Disease Control | Phyto-toxicity | Disease Control | Phyto-toxicity |
| 400 | 5 | 4[b] | 4+ | 0 |
| 100 | 5 | 3.5[b] | 4− | 0 |
| 25 | 5 | 0 | 3 | 0 |
| 6.25 | 5 | 0 | 2 | 0 |
| 0[c] | 1 | 0 | 1 | 0 |

[a]Average of two replicates
[b]Evidence of chlorosis
[c]Control

In order to illustrate this invention more fully, the following examples are provided.

EXAMPLE 1

The starting material is a blue-green alga species, *Lyngbya majuscula*, which can be collected in the lagoon on Enewetak atoll. The *L. majuscula* used in this Example was collected from Reefer 8 Pinnacle, Enewetak lagoon, at depths of from about 35 to about 60 feet. The alga is reddish in color and grows in hairlike strands. The alga is rinsed with sea water to eliminate major contaminating organisms.

Frozen *L. majuscula* (3 kg wet weight) thus collected was homogenized and extracted with a mixture of chloroform and methanol (1:2 by volume). Water was added to the filtrate; the chloroform layer was washed repeatedly with water, then was dried over anhydrous sodium sulfate and evaporated to give a crude extract (22 g). This extract (dissolved in chloroform) was chromatographed over a 4.7-×40-cm Florisil column (<200 mesh).

The column was developed with hexane (400 ml), hexane:chloroform mixtures (9:1–200 ml; 3:1–300 ml; 1:1–400 ml), chloroform (400 ml) and chloroform:methanol mixtures (9:1–400 ml; 3:1–400 ml; 1:1–200 ml). The following fractions were collected:

| Fraction No. | Volume (ml) |
|---|---|
| 0 | 250 |
| 1 | 300 |
| 2 | 150 |
| 3 | 300 |
| 4 | 250 |
| 5 | 250 |
| 6 | 225 |
| 7 | 250 |
| 8 | 250 |
| 9 | 600 |
| 10 | 250 |

Fractions 5 and 6, collected using hexane:chloroform (1:1) and chloroform, provided, after evaporation, 2.14 g and 1.94 g of substantially pure majusculamide C, respectively.

Subsequent development of the Florisil column, using chloroform:methanol (9:1), gave crude debromoaplysiatoxin which was purified over a silica gel column to give 400 mg of pure debromoaplysiatoxin.

Chromatography of fraction #5 from the Florisil column over a 1.5-cm×1.15-m column of Sephadex LH-20, eluting with chloroform:methanol (1:1) and collecting fractions based on proton magnetic resonance data, gave first fatty compounds and chlorophyll and then gave majusculamide C in an especially pure form (1.69 g).

EXAMPLE 2

The *L. majuscula* used in this experiment was collected at Enewetak from the South Medren Pinnacle in Enewetak lagoon in depths ranging from 35 to 60 feet. Freeze-dried *L. majuscula* (748 g) was exhaustively extracted with hexane, acetone, and methanol, respectively; the extracts were combined and dried to give 19 g of extract. This crude extract was partitioned between hexane (500 ml) and 90% methanol (100 ml). The resulting methanol layer was diluted with water and then was extracted with dichloromethane (500 ml). The dichloromethane was evaporated to give 4.8 g of brown semisolid which represented 25% of the crude extract, or 0.6% of the dried seaweed.

Majusculamide C was isolated from the dichloromethane extract by gel filtration. A portion of the dichloromethane extract (1.5 to 2 g) was filtered through a 180-×2.5-cm LH-20 Sephadex column, using $CH_2Cl_2$:$CH_3OH$ (1:1) as the solvent system and collecting 50-ml fractions. Crude majusculamide C was eluted in the third fraction.

Majusculamide C was further purified by HPLC with a Whatman Partisil ODS-2 reverse phase column. Purification was achieved using 30 mg of crude majusculamide C, a $CH_3CN$:$H_2O$ (7:3) mobile phase, a pressure of 300 psi and a flow rate of 1 ml per minute. Majusculamide C was retained for about 100 to 110 minutes. The eluant yielded a clear amorphous solid upon evaporation.

We claim:

1. Majusculamide C, which is a white amorphous solid having these characteristics:

(a) a molecular weight of approximately 984;
 (b) an empirical formula of about $C_{50}H_{80}N_8O_{12}$;
 (c) a specific optical rotation, $[\alpha]_D$, of $-96°$ (c 2.5, $CH_2Cl_2$);
 (d) an infrared spectrum as shown in the accompanying drawing;
 (e) an ultraviolet absorption spectrum in ethanol with absorption maxima at 278 nm ($\epsilon$ 1420) and 230 nm ($\epsilon$ 5900);
 (f) is soluble in solvents such as methanol, dichloromethane, and acetone, but is insoluble in water;
 (g) contains the structural sub-units 1a–1h:

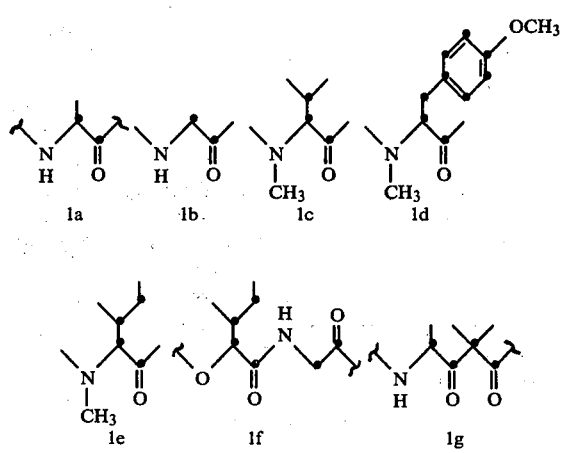

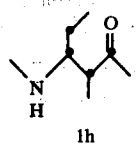

1h (h) appears to contain the sub-unit grouping: glycyl-N-methylisoleucylglycyl-N-methylvalyl-N,O-dimethyltyrosyl; and (i) the following tentative structure:

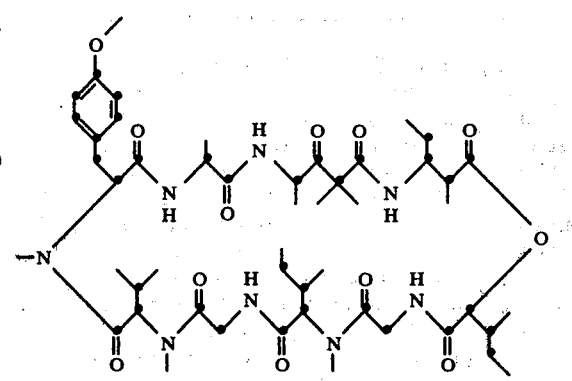

2

2. A process to produce the compound of claim 1 which comprises treating a deep-water algal association containing as its primary constituent the blue-green alga *Lyngbya majuscula*, which process comprises extracting the alga with an organic solvent in which the compound is soluble and thereafter isolating the compound by chromatography.

3. A method of inhibiting a plant-pathogenic fungus which comprises applying an effective amount of the compound of claim 1 to the locus of the fungus.

4. A composition suitable for inhibiting plant-pathogenic fungi comprising (1) an effective amount of a compound of claim 1 and (2) a suitable carrier.

* * * * *

UNITED STATES PATENT AND TRADEMARK OFFICE
CERTIFICATE OF CORRECTION

PATENT NO. : 4,342,751

DATED : August 3, 1982

INVENTOR(S) : Richard E. Moore and Jon S. Mynderse

It is certified that error appears in the above—identified patent and that said Letters Patent is hereby corrected as shown below:

Cover page, "[73] Assignee: Eli Lilly and Company, Indianapolis, Ind." should read --/73/ Assignee: The University of Hawaii, Honolulu, Hawaii --.

Column 11, lines 27-43, the structural formulas reading

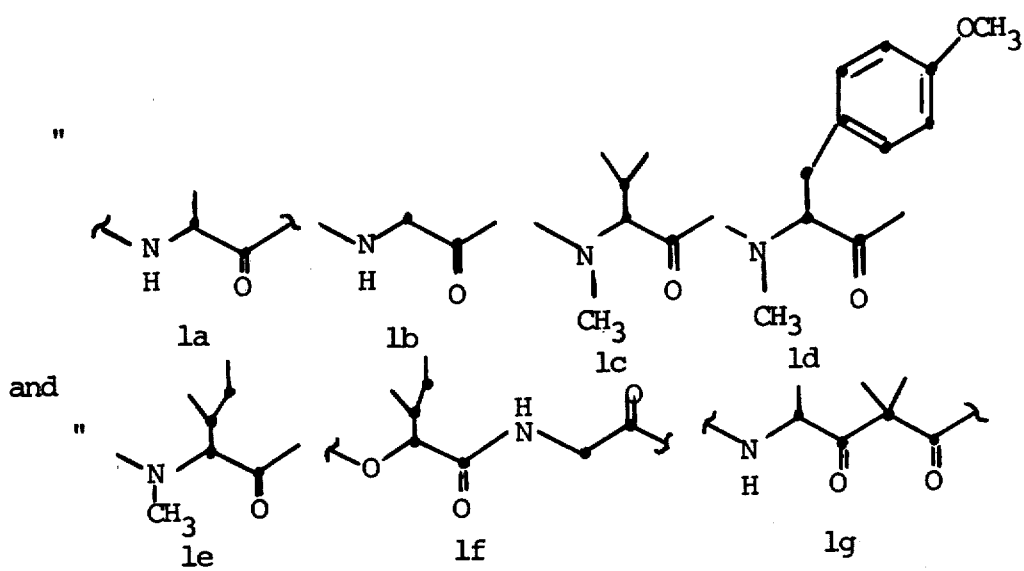

UNITED STATES PATENT AND TRADEMARK OFFICE
CERTIFICATE OF CORRECTION

PATENT NO. : 4,342,751

Page 2 of 3

DATED : August 3, 1982

INVENTOR(S) : Richard E. Moore and Jon S. Mynderse

It is certified that error appears in the above—identified patent and that said Letters Patent is hereby corrected as shown below:

should read

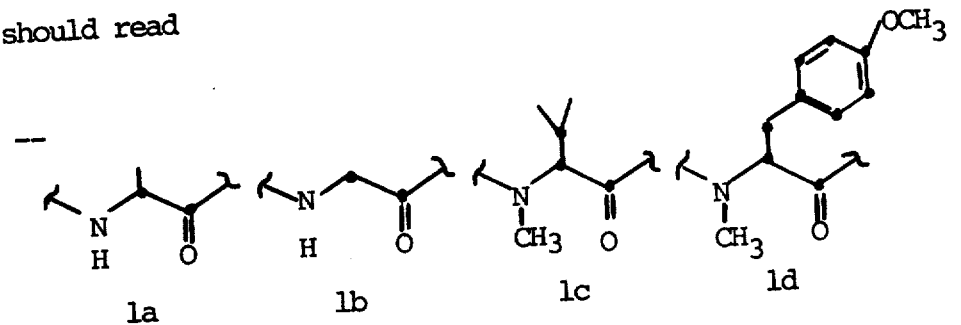

and

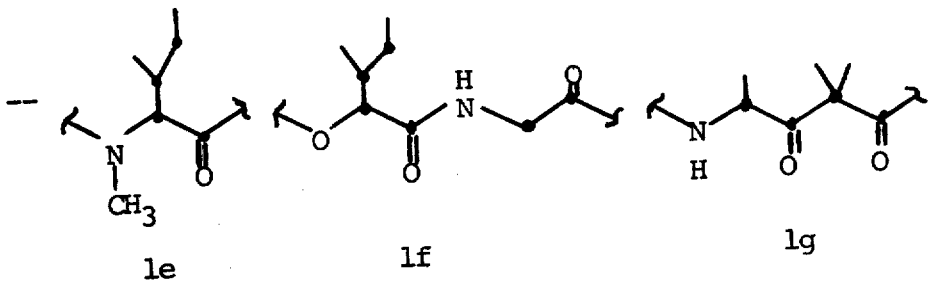

UNITED STATES PATENT AND TRADEMARK OFFICE
CERTIFICATE OF CORRECTION

PATENT NO. : 4,342,751

DATED : August 3, 1982

INVENTOR(S) : Richard E. Moore and Jon S. Mynderse

It is certified that error appears in the above—identified patent and that said Letters Patent is hereby corrected as shown below:

Column 12, lines 1-8, the first structural formula reading

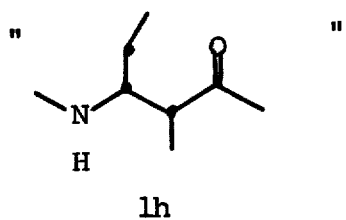

should read

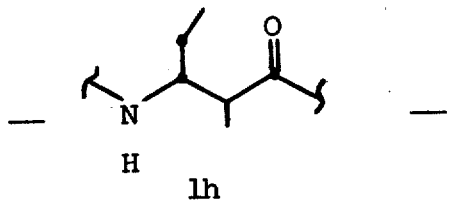

Signed and Sealed this

Twenty-eighth Day of December 1982

[SEAL]

Attest:

GERALD J. MOSSINGHOFF

Attesting Officer

Commissioner of Patents and Trademarks